United States Patent
Gade et al.

(10) Patent No.: US 12,042,500 B2
(45) Date of Patent: Jul. 23, 2024

(54) MUCOADHESIVE DRUG DELIVERY SYSTEM FOR OCULAR ADMINISTRATION OF FLUOROQUINOLONE ANTIBIOTICS

(71) Applicants: HYDERABAD EYE RESEARCH FOUNDATION, Telangana (IN); BIRLA INSTITUTE OF TECHNOLOGY AND SCIENCE (BITS) PILANI, Telangana (IN)

(72) Inventors: Sudeep Kumar Gade, Telangana (IN); Prashant Garg, Telangana (IN); Venkata Vamsi Krishna Venuganti, Telangana (IN)

(73) Assignees: HYDERABAD EYE RESEARCH FOUNDATION, Telangana (IN); BIRLA INSTITUTE OF TECHNOLOGY AND SCIENCE (BITS) PILANI, Telangana (IN)

( * ) Notice: Subject to any disclaimer, the term of this patent is extended or adjusted under 35 U.S.C. 154(b) by 392 days.

(21) Appl. No.: 17/044,922

(22) PCT Filed: Apr. 3, 2019

(86) PCT No.: PCT/IB2019/052725
§ 371 (c)(1),
(2) Date: Oct. 2, 2020

(87) PCT Pub. No.: WO2019/193513
PCT Pub. Date: Oct. 10, 2019

(65) Prior Publication Data
US 2021/0038612 A1    Feb. 11, 2021

(30) Foreign Application Priority Data
Apr. 3, 2018  (IN) .............................. 201841012721

(51) Int. Cl.
| *A61K 31/55* | (2006.01) |
| *A61K 9/00* | (2006.01) |
| *A61K 31/5383* | (2006.01) |
| *A61K 47/32* | (2006.01) |
| *A61K 47/36* | (2006.01) |
| *A61K 47/46* | (2006.01) |
| *A61P 31/04* | (2006.01) |

(52) U.S. Cl.
CPC ............ *A61K 31/55* (2013.01); *A61K 9/0048* (2013.01); *A61K 31/5383* (2013.01); *A61K 47/32* (2013.01); *A61K 47/36* (2013.01); *A61K 47/46* (2013.01); *A61P 31/04* (2018.01)

(58) Field of Classification Search
CPC .. A61K 31/55; A61K 9/0048; A61K 31/5383; A61K 47/32; A61K 47/36; A61K 47/46; A61K 31/47; A61K 31/722; A61P 31/04; A61P 27/02
See application file for complete search history.

(56) References Cited

U.S. PATENT DOCUMENTS

| 2001/0049366 A1* | 12/2001 | Singh | .................... A61K 31/56 514/171 |
| 2005/0244502 A1* | 11/2005 | Mathias | ............... A61K 9/0043 424/487 |

FOREIGN PATENT DOCUMENTS

| DE | 699 12 972 T2 | 4/2004 | |
| DE | 69912972 | * 4/2004 | .......... A61K 31/435 |
| KR | 100440239 B1 | * 7/2004 | ............... A61K 9/00 |
| WO | 2004/089418 A1 | 10/2004 | |
| WO | WO-2004089418 A1 | * 10/2004 | .......... A61K 31/496 |
| WO | 2008/157614 A1 | 12/2008 | |
| WO | WO-2008157614 A2 | * 12/2008 | .......... A61K 9/0048 |
| WO | 2017/024282 A1 | 2/2017 | |
| WO | WO-2017024282 A1 | * 2/2017 | .......... A61K 31/407 |

OTHER PUBLICATIONS

Teweldemedhin. BMC Ophthalmology, 2017, 17:212 (Year: 2017).*
Przemystaw Baranowski et al., "Ophthalmic Drug Dosage Forms: Characterisation and Research Methods", Scientific World Journal, Mar. 18, 2014, pp. 1-14.
ISR issued in WIPO Patent Application No. PCT/IB2019/052725, dated Aug. 2, 2019, English translation.
IPRP issued in WIPO Patent Application No. PCT/IB2019/052725, dated Aug. 2, 2019, English translation.

* cited by examiner

*Primary Examiner* — Susanna Moore
*Assistant Examiner* — Luisalberto Gonzalez
(74) *Attorney, Agent, or Firm* — GREENBLUM & BERNSTEIN, P.L.C.

(57) ABSTRACT

The present disclosure relates to ocular mucoadhesive pharmaceutical compositions comprising fluoroquinolone antibiotic, chitosan, polyvinyl alcohol and polyvinylpyrrolidone, their uses and methods of using such compositions.

18 Claims, 4 Drawing Sheets

MUCOADHESIVE DRUG DELIVERY SYSTEM FOR OCULAR ADMINISTRATION OF FLUOROQUINOLONE ANTIBIOTICS

CROSS-REFERENCE TO RELATED APPLICATION

This application claims the benefit of priority to Indian Provisional Patent Application number 201841012721, filed on Apr. 3, 2018, which is hereby incorporated by reference herein in its entirety.

TECHNICAL FIELD

The present subject matter disclosed herein, in general, relates to compositions and methods for ocular delivery of therapeutic agents. In particular, the subject matter relates to mucoadhesive pharmaceutical compositions comprising a fluoroquinolone antibiotic, chitosan, polyvinyl alcohol, polyvinylpyrrolidone; their uses and methods of using such compositions.

BACKGROUND

Fluoroquinolone antibiotics are well-known for treating ophthalmic infections such as keratitis, blepharitis, conjunctivitis and endophthalmitis. However, despite the general efficacy of the ophthalmic quinolone therapies currently available, several constraints are associated with the formulation of ocular drug delivery systems. The major challenge is to achieve an optimal concentration of a drug at the active site for the appropriate duration to provide ocular delivery systems with high therapeutic efficacy. Due to physiological and anatomical constraints such as solution drainage, lacrimation, tear dynamics, tear dilution, tear turnover, conjunctival absorption, nonproductive absorption, transient residence time in the cul-de-sac, and the relative impermeability of the corneal epithelial membrane, only a small fraction of the drug (only 5% or less of the instilled dose) is ocularly absorbed.

Therefore, there is a continuous need in the art to increase the bioavailability and the duration of the therapeutic action of ocular drugs. Also, there is a need for improved compositions and methods of treatment based on the use of antibiotics that are more effective than existing antibiotics against key ophthalmic pathogens, and less prone to the development of resistance by those pathogens.

Mucoadhesive pharmaceutical compositions comprising fluoroquinolone antimicrobial(s) are described in the present disclosure for addressing one or more problems in the ocular drug delivery including those disclosed above.

SUMMARY

The present disclosure relates to ocular mucoadhesive pharmaceutical compositions comprising a fluoroquinolone antibiotic, chitosan, polyvinyl alcohol and polyvinylpyrrolidone. The compositions are useful in the treatment and/or prophylaxis of eye diseases especially eye infections and/or inflammatory conditions of the eye.

In another aspect, the disclosure also provides a kit comprising any of the pharmaceutical compositions disclosed herein. The kit may comprise instructions for use in in the treatment and/or prophylaxis of eye diseases.

In yet another aspect, the disclosure also provides a method of treatment and/or prophylaxis of eye diseases in a subject comprising administering to the subject in need thereof a therapeutically effective amount of the pharmaceutical composition(s) as described herein.

BRIEF DESCRIPTION OF THE ACCOMPANYING FIGURES

DETAILED DESCRIPTION

Figure 1:
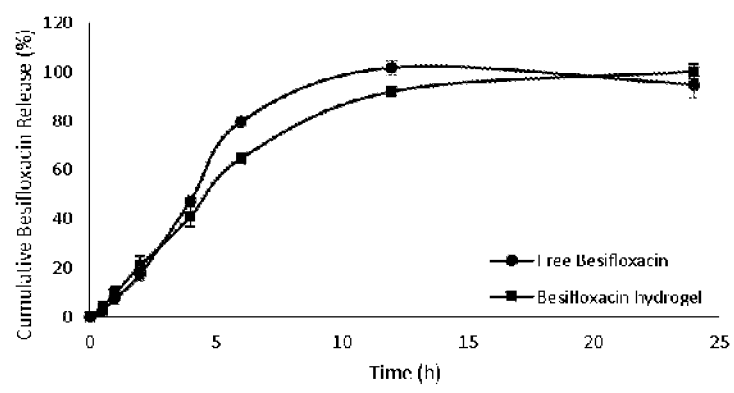
FIG. 1 illustrates in vitro release profiles of (a) besifloxacin and (b) levofloxacin from free drug solution and fluoroquinolones incorporated in hydrogel.
Figure 1:
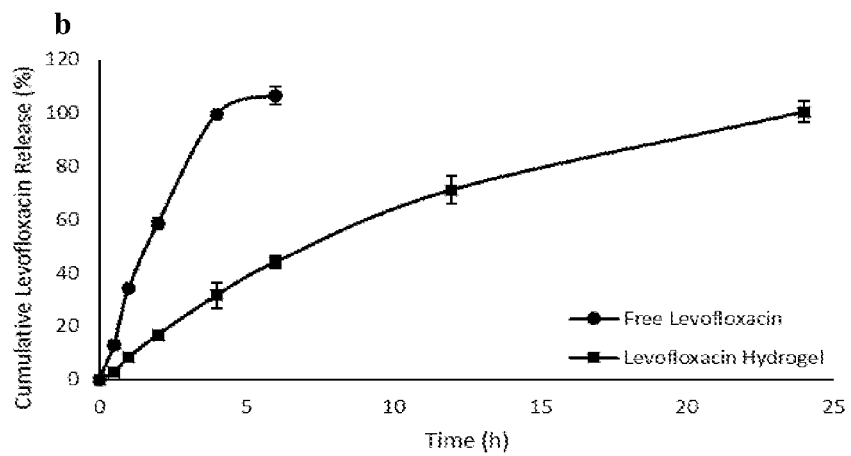

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Disclosed herein are ocular mucoadhesive pharmaceutical compositions comprising a therapeutically effective amount of fluoroquinolone antibiotic and a combination of polymers. The compositions disclosed herein show enhanced corneal mucoadhesion and permeation of besifloxacin and levofloxacin and advantageous over the currently available eye drops (Besix® and Levotop®) for ocular delivery of besifloxacin and levofloxacin.

Fluoroquinolone antibiotics of interest include, but are not limited to: balofloxacin, besifloxacin, cinoxacin, ciprofloxacin, clinafloxacin, danofloxacin, delafloxacin, diflofloxacin, enoxacin, enrofloxacin, fleroxacin, flumequine, gatifloxacin, gemifloxacin, grepafloxacin, ibafloxacin, JNJ-Q2, levofloxacin, lomefloxacin, marbofloxacin, moxifloxacin, nadifloxacin, nalidixic acid, nemonoxacin, norfloxacin, ofloxacin, orbifloxacin, oxilinic acid, pazufloxacin, pefloxacin, piromidic acid, pipemidic acid, prulifloxacin, rosoxacin, rufloxacin, sarafloxacin, sparfloxacin, sitafloxacin, temafloxacin, tosufloxacin and trovafloxacin, or a pharmaceutically acceptable salt or a stereoisomer thereof.

In certain embodiments, the polymers are selected from the group comprising chitosan, polyvinyl alcohol (PVA) and polyvinylpyrrolidone (PVP). In further embodiments, the pharmaceutical composition comprises three polymers: chitosan, PVA and PVP.

The composition may further comprise one or more permeation enhancers. In certain embodiments, the permeation enhancer is selected from a group comprising lysophosphatidilo lipids (lysophosphatidylcholine, LPC), calcium chelators (EDTA), benzalkonium chloride, cetylpyridinium chloride, palmitoyl carnitine, non-ionic surfactants (Brij 35, Brij 78, Brij 98, sodium deoxycholate, poly oxyethylene-9-lauryl ether), surface-active heteroglycosides and bile salts (deoxycholate, taurodeoxycholate, and glycocholate), and glycosides (saponins, digitonin, caprylic acid, capric acid).

It is to be contemplated that when a particular compound is mentioned by name, for example, levofloxacin or besifloxacin, the scope of the present disclosure encompasses pharmaceutically acceptable salts, stereoisomers, esters, amides, or prodrugs of the named compound. Further, when the named compound comprises a chiral center the scope of the present disclosure also includes compositions comprising the racemic mixture of the two enantiomers, as well as compositions comprising each enantiomer individually substantially free of the other enantiomer. In further embodiments, if the named compound comprises more than one chiral center, the scope of the present disclosure also includes compositions comprising a mixture of the various diastereomers, as well as compositions comprising each diastereomer substantially free of the other diastereomers. For example, if commercially available fluoroquinolone antibiotic comprises two stereocenters, the scope of the present disclosure includes pharmaceutical compositions comprising all four diastereomers, pharmaceutical compositions comprising the racemic mixture of R,R and S,S isomers, pharmaceutical compositions comprising the racemic mixture of R,S and S,R isomers, pharmaceutical compositions comprising the R,R enantiomer substantially free of the other diastereomers, pharmaceutical compositions comprising the S,S enantiomer substantially free of the other diastereomers, pharmaceutical compositions comprising the R,S enantiomer substantially free of the other diastereomers, and pharmaceutical compositions comprising the S,R enantiomer substantially free of the other diastereomers.

In certain embodiments, the composition comprising R enantiomer is substantially free of S enantiomer, or a composition comprising S enantiomer is substantially free of R enantiomer. In this context, "substantially free" means, the composition comprises less than about 20%, or less than about 15%, or less than about 10%, or less than about 5%, or less than about 3% or less than about 1% of the minor enantiomer.

In certain embodiments, the present disclosure discloses a mucoadhesive pharmaceutical compositions comprising a therapeutically effective amount of fluoroquinolone antibiotic, chitosan, PVA, PVP and LPC.

In certain embodiments, fluoroquinolone antibiotic is present in an amount from about 0.01 to about 1 wt. %. In further embodiments, fluoroquinolone antibiotic is present in an amount from about 0.3 to about 0.6 wt. %.

In certain embodiments, the chitosan is present in an amount from about 0.2 to about 3 wt. %. In further embodiments, the chitosan is present in an amount from about 0.5 to about 2 wt. %.

In certain embodiments, the PVA is present in an amount from about 0.2 to about 8 wt. %. In further embodiments, the PVA is present in an amount from about 0.5 to about 5 wt. %.

In certain embodiments, the PVP is present in an amount from about 0.5 to about 8 wt. %. In further embodiments, the PVP is present in an amount from about 0.5 to about 5 wt. %.

In certain embodiments, the LPC is present in an amount from about 0.01 to about 2 wt. %. In further embodiments, the LPC is present in an amount from about 0.05 to about 1 wt. %.

In certain embodiments, the pharmaceutical composition comprises:
  fluoroquinolone antibiotic in an amount from about 0.3 to about 0.6% w/v;
  chitosan in an amount from about 0.5 to about 2% w/v;
  PVA in an amount from about 0.5 to about 5% w/v;
  PVP is in an amount from about 0.5 to about 5% w/v; and
  LPC in an amount from about 0.05 to about 0.5% w/v.

The composition may be formulated as a topical solution, suspension, gel, emulsion, ointment, insert or film. In certain embodiments, the compositions as disclosed herein may be administered in the form of eye drops, eye washes, eye ointment, eye creams, ophthalmic gels and the like. The composition may be in unit dosage form for administration of a single dose or it may be in a dosage form containing more than one dose.

In certain embodiments, disclosed herein is a hydrogel composition comprising a therapeutically effective amount of fluoroquinolone antibiotic, chitosan, PVA and PVP. The hydrogel composition may further comprise one or more permeation enhancers.

The fluoroquinolone antibiotic and permeation enhancer are as defined above. In certain embodiments, the fluoroquinolone antibiotic is selected from a group comprising besifloxacin, ciprofloxacin, ofloxacin, levofloxacin, gatifloxacin and moxifloxacin. In further embodiments, the fluoroquinolone antibiotic is besifloxacin or levofloxacin or a combination thereof.

In certain embodiments, the hydrogel composition comprises a therapeutically effective amount of besifloxacin, chitosan, PVA, PVP and, optionally, LPC.

In certain embodiments, the hydrogel composition comprises a therapeutically effective amount of levofloxacin, chitosan, PVA, PVP and, optionally, LPC.

In certain embodiments, the hydrogel composition comprises fluoroquinolone antibiotic in an amount from about 0.01 to about 1% w/v. In further embodiments, the fluoroquinolone antibiotic is present in an amount from about 0.1 to about 0.8% w/v, such as from about 0.3 to about 0.6% w/v, including about 0.35% w/v or about 0.4% w/v or about 0.45% w/v or about 0.5% w/v about or 0.55% w/v. In some instances, the fluoroquinolone antibiotic is besifloxacin or levofloxacin or a combination thereof.

In certain embodiments, the hydrogel composition comprises chitosan in an amount from about 0.2 to about 3% w/v. In further embodiments, the chitosan is present in an amount from about 0.5 to about 2% w/v, such as from 0.5 to about 1.5% w/v, including about 0.6% w/v or about 0.7% w/v or about 0.8% w/v or about 0.9% w/v or about 1.0% w/v or about 1.1% w/v or about 1.2% w/v or about 1.3% w/v or about 1.4% w/v. In some instances, the chitosan may have any suitable molecular weight, for example, about 1-1000 kDa, such as 1-500 kDa, including, about 2 kDa or about 4 kDa or about 5 kDa or about 8 kDa or about 9 kDa or about 10 kDa or about 12 kDa or about 15 kDa or about 20 kDa or about 25 kDa or about 30 kDa or about 40 kDa or about 45 kDa or about 50 kDa or about 55 kDa or about 60 kDa or about 65 kDa or about 70 kDa or about 75 kDa or about 80 kDa or about 85 kDa or about 90 kDa or about 95 kDa or about 100 kDa or about 110 kDa or about 120 kDa or about 130 kDa or about 140 kDa or about 150 kDa or about 160 kDa or about 170 kDa or about 180 kDa or about 190 kDa or about 200 kDa or about 220 kDa or about 240 kDa or about 260 kDa or about 280 kDa or about 300 kDa or about 320 kDa or about 340 kDa or about 360 kDa or about 380 kDa, or about 400 kDa or about 420 kDa, or about 480 kDa. In certain embodiments, the hydrogel composition may comprise chitosan polymers of different molecular weights. The chitosan used may be deacetylated chitosan. In certain embodiments, the degree of deacetylation may range from, but is not limited to, about 50% or more deacetylation, such as 50-99% deacetylation, including about 50-90% deacetylation, or about 55-85% deacetylation or about 60-85% deacetylation or about 70-85% deacetylation or about 80-85% deacetylation.

In certain embodiments, the hydrogel composition comprises polyvinyl alcohol (PVA) in an amount from about 0.2 to about 8% w/v. In further embodiments, the PVA is present in an amount from about 0.2 to about 7% w/v, such as from about 0.5 to about 5% w/v, including, about 0.6% w/v or about 0.7% w/v or about 0.8% w/v or about 0.9% w/v, or about 1.0% w/v or about 1.2% w/v or about 1.4% w/v or about 1.6% w/v or about 1.8% w/v or about 2.0% w/v or about 2.2% w/v or about 2.4% w/v or about 2.6% w/v or about 2.8% w/v or about 3.0% w/v or about 3.2% w/v or about 3.6% w/v or about 3.8% w/v or about 4.0% w/v or about 4.2% w/v or about 4.4% w/v or about 4.6% w/v or about 4.8% w/v. In some instances, the PVA may have any suitable molecular weight, for example, about 1-1000 kDa, such as 1-500 kDa, including, about 2 kDa or about 3 kDa or about 4 kDa or about 5 kDa or about 8 kDa or about 9 kDa or about 10 kDa or about 12 kDa or about 15 kDa or about 20 kDa or about 25 kDa or about 30 kDa or about 40 kDa or about 45 kDa or about 50 kDa or about 55 kDa or about 60 kDa or about 65 kDa or about 70 kDa or about 75 kDa, or about 80 kDa or about 85 kDa or about 90 kDa or about 95 kDa or about 100 kDa or about 110 kDa or about 120 kDa or about 130 kDa or about 140 kDa or about 150 kDa or about 160 kDa or about 170 kDa or about 180 kDa or about 190 kDa or about 200 kDa or about 210 kDa or about 250 kDa or about 300 kDa or about 350 kDa or about 400 kDa or about 450 kDa.

In certain embodiments, the hydrogel composition comprises polyvinylpyrrolidone (PVP) in an amount from about 0.5 to about 8% w/v. In further embodiments, the PVP is present in an amount from about 0.5 to about 5% w/v. In yet further embodiments, the PVP is present in an amount of about 1% w/v or about 1.5% w/v or about 2.0% w/v or about 2.5% w/v or about 3.0% w/v or about 3.5% w/v or about 4.0% w/v or about 4.5% w/v. In some instances, the PVP may have any suitable molecular weight, for example, about 1-1000 kDa, such as 1-500 kDa and 1-250 kDa, including, about 2 kDa or about 4 kDa or about 5 kDa or about 8 kDa or about 9 kDa or about 10 kDa or about 12 kDa or about 15 kDa or about 20 kDa or about 25 kDa or about 30 kDa or about 40 kDa or about 45 kDa or about 50 kDa or about 55 kDa or about 60 kDa or about 65 kDa or about 70 kDa or about 75 kDa or about 80 kDa or about 85 kDa or about 90 kDa or about 95 kDa or about 100 kDa or about 110 kDa or about 120 kDa or about 130 kDa or about 140 kDa or about 150 kDa or about 160 kDa or about 170 kDa or about 180 kDa or about 190 kDa or about 200 kDa or about 210 kDa or about 220 kDa or about 230 kDa or about 240 kDa. In certain embodiments, the PVP polymer may be homopolymeric PVP and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum.

In certain embodiments, the hydrogel composition comprises LPC in an amount from about 0.01 to about 2% w/v. In further embodiments, the LPC is present in an amount from about 0.01 to about 1.5% w/v, such as from about 0.01 to about 1.0% w/v, including from about 0.05 to about 0.5% w/v, e.g., about 0.1% w/v or about 0.2% w/v or about 0.3% w/v or about 0.4% w/v or about 0.5% w/v or about 0.6% w/v or about 0.7% w/v or about 0.8% w/v or about 0.9% w/v.

In certain embodiments, the hydrogel composition comprises:
  fluoroquinolone antibiotic in an amount from about 0.3 to about 0.6% w/v;
  chitosan in an amount from about 0.5 to about 2% w/v;
  PVA in an amount from about 0.5 to about 5% w/v;
  PVP is in an amount from about 0.5 to about 5% w/v; and
  LPC in an amount from about 0.05 to about 0.5% w/v.

The compositions as disclosed herein may further comprise a pharmaceutically acceptable carrier excipient. Examples of pharmaceutically acceptable excipients include, but are not limited to solvents such as water, pH adjusting agents such as sodium hydroxide and hydrochloric acid, isotonic adjusting agents such as glycerol, mannitol, sorbitol, xylitol and the like, gelling agents such as cellulose derivatives (e.g., hydroxyethylcellulose, hydroxypropylmethylcellulose and the like) and polymers from the Pluronic® series, viscosity-adjusting agents such as hydroxyethylcellulose and hydroxypropylmethylcellulose, preservatives like, e.g., benzalkonium chloride, parabenes, chlorohexidine, chlorohexidine gluconate and chlorohexidine acetate, chelating agents such as EDTA, stabilisers/antioxidants such as tocopherol, tocopherol acetate, butylhydroxytoluene and butylhydroxyanisol.

The compositions as disclosed herein can be used as a medicament. In certain embodiments, the compositions are useful in the treatment and/or prophylaxis of eye diseases especially eye infections and/or inflammatory conditions of the eye. In certain embodiments, the compositions as disclosed herein are useful for treating ophthalmic infections such as keratitis, blepharitis, conjunctivitis and endophthalmitis.

In certain embodiments, the disclosure also provides a kit comprising any of the pharmaceutical compositions disclosed herein. The kit may comprise instructions for use in in the treatment and/or prophylaxis of eye diseases.

The present disclosure also provides a mucoadhesive-based ophthalmic drug delivery system comprising a hydrogel composition as disclosed herein. The mucoadhesive drug delivery system is useful in a method of delivering one or more pharmacologically active agents through the ocular tissue of a subject. In certain embodiments, the ocular tissue is corneal tissue. In certain embodiments, the method comprises adhering the mucoadhesive drug delivery system to the corneal tissue of a subject.

The present disclosure also describes a method of treatment and/or prophylaxis of an eye disease or an ocular condition, disease, or condition in a subject comprising administering to the subject in need thereof a therapeutically effective amount of the pharmaceutical composition(s) as described herein. In certain embodiments, the present disclosure describes a method for treating an ocular condition, disease, or condition in a subject comprising administering to target site of an eye of a subject a composition as described herein. The ocular condition is selected from a group comprising blepharitis, conjunctivitis, keratitis, endophthalmitis and those conditions caused by Gram-positive and Gram-negative bacteria, such as *Staphylococcus aureus, Staphylococcus epidermidis* and *Pseudomonas aeruginosa*.

The compositions, e.g., as described herein, may be administered to a variety of different types of subjects. Subjects of interest include, but are not limited to: mammals, both human and non-human, including the orders carnivore (e.g., cats and dogs), rodentia (e.g., mice, guinea pigs, and rats), lagomorpha (e.g. rabbits) and primates (e.g., humans, chimpanzees, and monkeys). In certain embodiments, the subject (e.g., patient) is human.

In certain embodiments, the composition as disclosed herein may inhibit growth of at least one pathogen selected from the group comprising *S. aureus, S. epidermidis, S. pneumoniae, P. aeruginosa*, and *H. influenzae*.

In certain embodiments, mucoadhesion of besifloxacin and levofloxacin hydrogels was 3.5 and 8-folds higher, respectively, compared with commercial eye drops and free drug solutions ($p<0.001$).

In certain embodiments, cumulative corneal permeation of hydrogel formulation is higher compared to that of commercially available besifloxacin and levofloxacin formulations.

In certain embodiments, the hydrogel compositions/formulations as disclosed herein showed enhanced mucoadhesion and superior permeation of fluoroquinolone antibiotic in to human cornea compared to commercial formulations. In a further embodiment, the hydrogel compositions as disclosed herein showed superior antibacterial activity.

In certain embodiments, the hydrogel compositions of fluoroquinolone antibiotics are formulated such that the hydrogel compositions may exhibit up to 100-fold higher mucoadhesion and superior cumulative corneal permeation as compared to commercial ophthalmic preparations and free drug solutions. In further embodiments, the hydrogel compositions/formulations of fluoroquinolone antibiotics of the present disclosure may exhibit about 1-50 fold, such as about 1-fold or about 1.5-fold or about 2-fold or about 2.5-fold or about 3-fold or about 3.5-fold or about 4-fold or about 4.5-fold or about 5-fold or about 5.5-fold or about 6-fold or about 6.5-fold or about 7.5-fold or about 8-fold or about 8.5-fold or about 9-fold or about 9.5-fold or about 10-fold or about 10.5-fold or about 11-fold or about 12-fold or about 12.5-fold or about 13-fold or about 13.5-fold or about 14-fold or about 14.5-fold or about 15-fold higher mucoadhesion and superior cumulative corneal permeation as compared to commercial ophthalmic preparations and free drug solutions.

In certain embodiments, compared to commercial ophthalmic preparations and free drug solutions the hydrogel compositions/formulations of besifloxacin and levofloxacin was found to have 3.5 and 8-folds higher ($p<0.001$) mucoadhesion and superior cumulative corneal permeation. The formulations showed superior in-vitro anti-infective properties. Incubation of besifloxacin and levofloxacin formulations with *Staphylococcus aureus* infected cornea model for 0.5 h showed greater potency of the hydrogel formulations compared to the marketed eye drops and standard solutions.

In certain embodiments, incubation of besifloxacin and levofloxacin hydrogel formulations/compositions of the present disclosure with *S. aureus* infected cornea for 0.5 h showed higher potency compared to the marketed eye drops and standard solutions.

The compositions as disclosed herein can be prepared by any method known in the art.

In certain embodiments, disclosed is a process of preparing a hydrogel composition comprising a fluoroquinolone antibiotic, chitosan, PVA, PVP, and optionally permeation enhancer. The process comprises: preparing multicomponent hydrogel comprising chitosan, polyvinyl alcohol, polyvinylpyrrolidone; and adding fluoroquinolone antibiotic to the multicomponent hydrogel. The process for preparing multicomponent hydrogel comprises treating chitosan with polyvinyl alcohol in an aqueous solution comprising acid; and adding polyvinylpyrrolidone followed by lysophosphatidylcholine. Any acid (organic or inorganic) suitable in the process can be employed in the process. In certain embodiments, chitosan is treated with polyvinyl alcohol in an acetic acid solution at a temperature of about 30-80° C.

Unless defined otherwise, all technical and scientific terms used herein have the same meaning and the meaning of such terms is independent at each occurrence thereof and is as commonly understood by one of skill in art to which the subject matter herein belongs. That notwithstanding and except where stated otherwise, the following definitions apply throughout the specification and claims.

As used herein, the term "comprise", "comprises" or "comprising" is generally used in the sense of include, that is to say permitting the presence of one or more additional (unspecified) features or components.

As used herein, the term "including" as well as other forms, such as "include", "includes," and "included," is not limiting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to a product obtained by reaction of the fluoroquinolone antibiotic of the present disclosure with a suitable acid or a base. Pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. The fluoroquinolone antibiotic may also form pharmaceutically acceptable salts with various organic bases such as lysine, arginine, guanidine, diethanolamine or metformin. Suitable base salts include, but are not limited to, aluminum, calcium, lithium, magnesium, potassium, sodium, and zinc salts.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "prophylactic" or "prophylaxis" or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

As used herein, the term "stereoisomer" is a term used for all isomers of individual compounds of the present disclosure that differ only in the orientation of their atoms in space. The term stereoisomer includes mirror image isomers (enantiomers) of compounds of the present disclosure, mixtures of mirror image isomers (racemates, racemic mixtures) of compounds of the present disclosure, geometric (cis/trans or E/Z, R/S) isomers of compounds of the present invention and isomers of compounds of the present disclosure with more than one chiral center that are not mirror images of one another (diastereoisomers).

The phrase "therapeutically effective amount" is an art-recognized term. In certain embodiments, the term refers to an amount of a solvate or hydrate or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The term "treating" is art-recognized and includes preventing a disease, disorder or condition from occurring in a subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating keratitis, blepharitis, conjunctivitis and endophthalmitis and other related diseases or any other medical condition, is well understood in the art, and includes administration of a composition which reduces the frequency of, or delays the onset of, symptoms of a medical condition in a subject relative to a subject which does not receive the composition.

The present invention is illustrated in the following examples, which should not be construed as limiting. Other objects, features, advantages and aspects of the present invention will become apparent to those of skill from the present description and examples. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

The source of all the materials, reagents and the compounds used in the present disclosure are as follows:

Besifloxacin HCl was supplied by R. V. Northland Institute, India as unconditional support for the study. Levofloxacin, poly(N-vinylpyrrolidone) (PVP K-30, MW: 40 kDa), chitosan (80-85% deacetylated, MW: 100-300 kDa), polyvinyl alcohol (PVA, MW: 140 kDa), potassium dihydrogen phosphate, dipotassium hydrogen phosphate, lyso-phosphatidylcholine, sodium chloride, potassium chloride, was obtained from Sigma Aldrich, India. Milli-Q (Millipore, USA) water was used for all the experiments. Marketed preparations of besifloxacin (Besix®) and levofloxacin (Levotop®) were used as control formulations. Excised human cornea was obtained from Ramayamma International Eye Bank, L V Prasad Eye Institute, Hyderabad, India. Cornea were transported in Dulbecco's Medium Eagle media and were stored at −20° C.

EXAMPLES

Preparation of Hydrogel Formulation:

STEP A: Preparation of Multicomponent hydrogel formulation containing chitosan, polyvinyl alcohol, polyvinylpyrrolidone polymers.

In the first step, chitosan (0.5-1% w/w) was added to the deionized water containing glacial acetic acid (0.5% v/v) with continuous stirring. To the above solution, polyvinyl alcohol (1-3% w/w) was added slowly. The temperature of the preparation was maintained at 55° C. for the dissolution of PVA. Polyvinylpyrrolidone (0.5-1% w/w) was added to this solution. Lysophophatidylcholine (0.05% w/w) was added in the final step.

STEP B: For preparation of fluoroquinolone containing hydrogel, 0.4% w/v of besifloxacin or levofloxacin was added to the blank hydrogel with continuous stirring. Table 1 shows the final composition of the formulation.

The hydrogel was prepared by conventional stirring method using the components listed in the Table 1. The concentration of the polymers was optimized to 5% (3% PVA: 1% PVP: 1% chitosan) for besifloxacin and 2% (1% PVA: 0.5% PVP: 0.5% chitosan) for levofloxacin, respectively. The pH values of besifloxacin and levofloxacin hydrogels were 6.29±0.001, 6.14±0.002 and 5.78±0.005, 5.75±0.002 with and without addition of LPC, respectively. Viscosity of the hydrogels were 139.93±1.70, 142.80±4.25 and 21.41±0.52, 22.09±1.79 for besifloxacin and levofloxacin formulations, respectively. Transparency of the hydrogels was >95% for besifloxacin and >98% for levofloxacin formulations.

Characterization of the Hydrogel Formulation:

The hydrogels were characterized for their physicochemical properties. pH was measured using digital pH meter (Elico Ltd., India). Viscosity of sample preparations was measured using cup and bob rheometer (Brookfield Inc., USA) after subjecting to different shear rates at 25±1° C. The percentage transmittance of the hydrogel was recorded between 400 and 700 nm wavelength using UV-visible spectrophotometer (Jasco Instruments, USA). The percentage drug content was estimated by dissolving 20 μl drug loaded hydrogel in 980 μl distilled water and the concentration was determined using high performance liquid chromatography (HPLC).

HPLC Method

HPLC analysis was performed using Shimadzu Prominence UFLC, LC-20 system (Shimadzu, Japan) with a C18 column (Shimpack GIST column, 5 μm, 4.6×250 mm). The mobile phase used for besifloxacin analysis comprised of a mixture of 0.5% triethylamine solution (pH adjusted to 3.0 with 10% ortho-phosphoric acid) and acetonitrile (ACN) (74:26, v/v) (Costa et al, 2014). For levofloxacin analysis, 20 mM potassium dihydrogen phosphate ($KH_2PO_4$) with 1.0 ml triethylamine solution (pH adjusted to 2.5 with 10% ortho-phosphoric acid) and acetonitrile (77:23, v/v) was used (Dabhi et al, 2013). The injection volume was 50 μl for all the standards and test solutions. The flow rate and column temperature were maintained at 1.0 ml/min and 25° C., respectively. Besifloxacin and levofloxacin were detected at $\lambda_{max(besifloxacin)}$=295 and $\lambda_{max(levofloxacin)}$=294, respectively. The amount of drug release was determined using respective standard calibration curves.

The composition and physicochemical properties of hydrogel formulations were depicted in Table 1 below.

TABLE 1

| Formulation | PVA (% w/v) | PVP (% w/v) | CHI (% w/v) | LPC (% w/v) | Drug (% w/v) | pH | Viscosity (cP) | Transparency (% T) | Drug content (%) |
|---|---|---|---|---|---|---|---|---|---|
| Besifloxacin hydrogel + LPC | 3.0 | 1.0 | 1.0 | 0.05 | 0.40 | 6.29 ± 0.001 | 139.93 ± 1.70 | 95.0 | 99.94 |
| Besifloxacin hydrogel − LPC | 3.0 | 1.0 | 1.0 | — | 0.40 | 6.14 ± 0.002 | 142.80 ± 4.25 | 96.0 | 101.67 |
| Levofloxacin hydrogel + LPC | 1.0 | 0.5 | 0.5 | 0.05 | 0.40 | 5.78 ± 0.005 | 21.41 ± 0.52 | 98.0 | 99.01 |
| Levofloxacin hydrogel − LPC | 1.0 | 0.5 | 0.5 | — | 0.40 | 5.75 ± 0.002 | 22.09 ± 1.79 | 98.0 | 99.22 |

In Vitro Drug Release Study

In vitro release of drugs was performed using Franz diffusion cell apparatus (Permegear Inc., USA). Dialysis membrane (molecular weight cut-off of 2.5-3.0 kDa, Himedia, India) was placed between donor and receptor compartments of the diffusion cell. Phosphate buffered saline (100 mM, pH 7.4) was used as a receptor medium and the temperature was maintained at 33±1° C. using heated water circulator. The donor compartment was loaded with 2 mg of drug containing polymeric hydrogel or standard drug solution or marketed formulation. Samples (300 μl) were withdrawn from the sampling port at predetermined time intervals 0.5, 1, 2, 4, 6, 12 and 24 h and replaced with fresh media. Samples were analyzed using HPLC method described above.

In Vitro Release of Besifloxacin and Levofloxacin

FIG. 1 shows the diffusion of free drug and drug release from hydrogel. Free besifloxacin diffused completely across the membrane within 10 h. On the other hand, 100% release of besifloxacin from hydrogel preparation was achieved in 24 h (FIG. 1a). Besifloxacin release from hydrogel preparation was initially higher (up to 2 h) compared with free drug. In the case of levofloxacin, 100% of drug concentration diffused within 2 h and 24 h for free drug and drug loaded hydrogel, respectively (FIG. 1b).

Mucoadhesion Test

Adhesive strength of hydrogel to mucus membrane was examined qualitatively using a method known in the art (Choy et. al, 2008). A dialysis membrane (PVDF membrane, 0.45 μm pore size) was soaked in an aqueous mucin solution (0.1% mucin from porcine stomach, Type II bound with sialic acid) for 2 h. Hydrogel (20 μl) containing rhodamine B (50 μg/ml) was applied as a single drop at the center of the membrane. The membrane was then immediately washed with PBS for 5 min. The number of remaining particles was measured using fluorescence microscope and spectrofluorometer.

In Vitro Mucoadhesion Test

Figure 2:
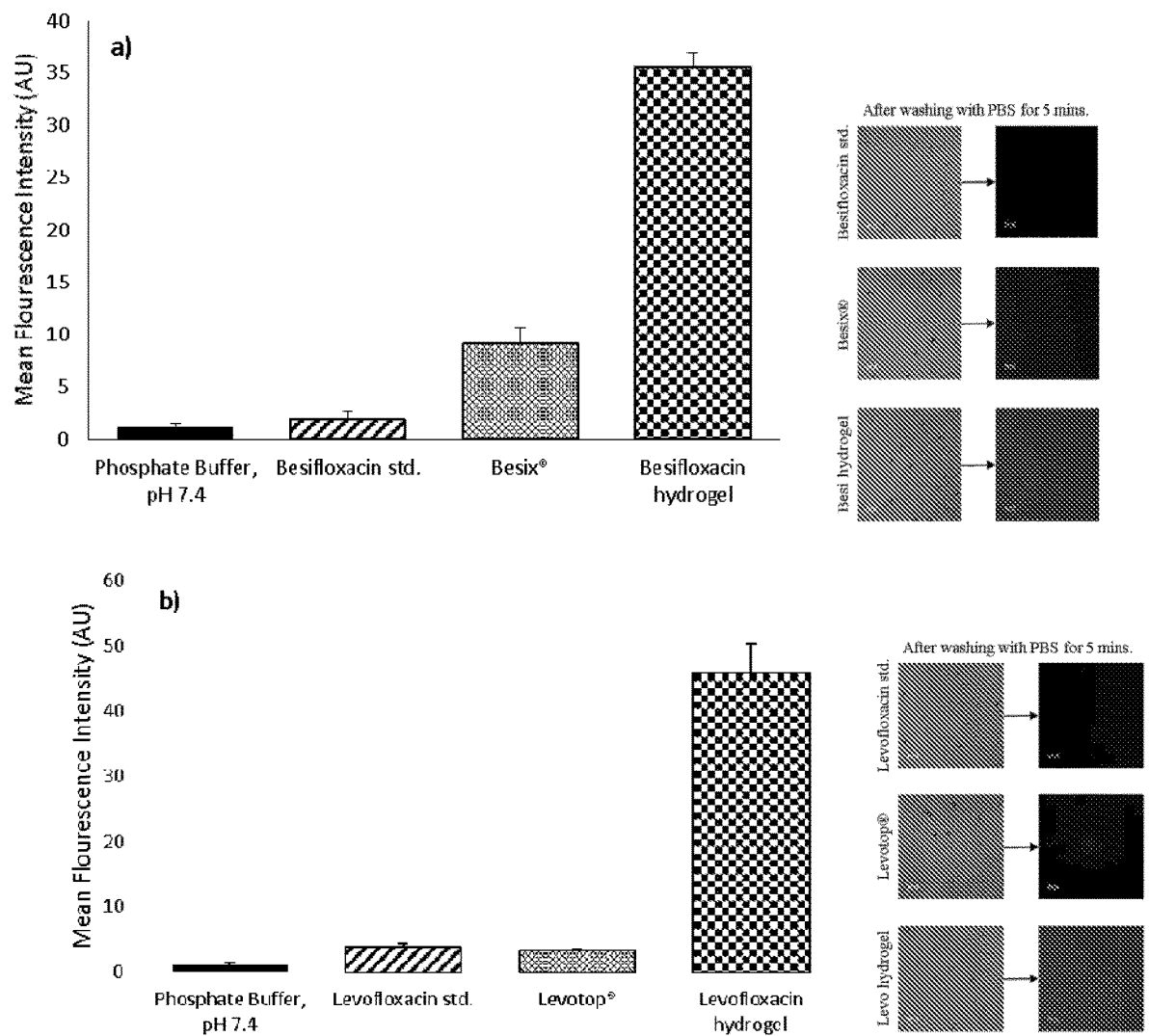
FIG. 2 illustrates in vitro mucoadhesion test. Mean fluorescence intensity of (a) besifloxacin and (b) levofloxacin formulations.

Mucoadhesion of besifloxacin and levofloxacin formulations was investigated in-vitro using dialysis membrane soaked in salicylic acid bound mucin to simulate ocular surface. Mucin surface was washed with PBS to simulate lacrimal secretions. As shown in FIG. 2, mucoadhesion of besifloxacin hydrogel was 3.5-fold and levofloxacin hydrogel was 8-fold higher as compared to marketed eye drops (p<0.001). Fluorescence micrographs show greater adhesion of hydrogel formulations on to cornea compared with free dye.

Ex Vivo Corneal Permeation of Antibiotics

Thickness of corneal membrane was measured using digital micrometer (Baker gauges India Pvt. Ltd., India). Corneal resistance (R) was measured by applying direct current (I, 1 mA) across the cornea using a DC power supply unit and the voltage drop (V) was measured using a digital multimeter (Fluke Corporation, USA). The resistance (R) was calculated using Ohm's law (V=IR).

Ex vivo corneal penetration of besifloxacin and levofloxacin was performed using Franz diffusion cell apparatus (PearmGear Corp., USA). Excised human cornea was washed with PBS and mounted between donor and receptor compartments with epithelial side facing donor chamber. Receptor medium contained PBS maintained at 37±1° C. temperature using heated water circulator unit. The donor compartment was charged with 0.4% of drug containing polymeric hydrogel, standard drug solution or marketed formulation. Samples (300 µl) were withdrawn from the receptor chamber at predetermined time intervals including 0.5, 1, 2, 4, 6, 12 and 24 h. Samples were analyzed by HPLC method described above. The amount of drug permeated was determined using respective standards (0.1, 1, 5, 10, 50 and 100 µg/ml) with $R^2$ of 0.999 for besifloxacin and R2 of 0.997 for levofloxacin. Corneal permeation parameters were calculated from cumulative amount of drug permeated vs. time profile. Flux (J) was calculated from the slope of the linear portion of cumulative amount of permeated vs. time profile. Lag time ($t_{lag}$) was calculated by extrapolating the linear portion of the curve to time axis. Permeability coefficient (Kp) was calculated using Equation 1.

$$\text{Permeability coefficient } (Kp) = \frac{\text{Flux}}{\text{Concentration of } FQ} \quad (1)$$

In-Vitro Corneal Permeation of Besifloxacin and Levofloxacin Formulations

Figure 3:
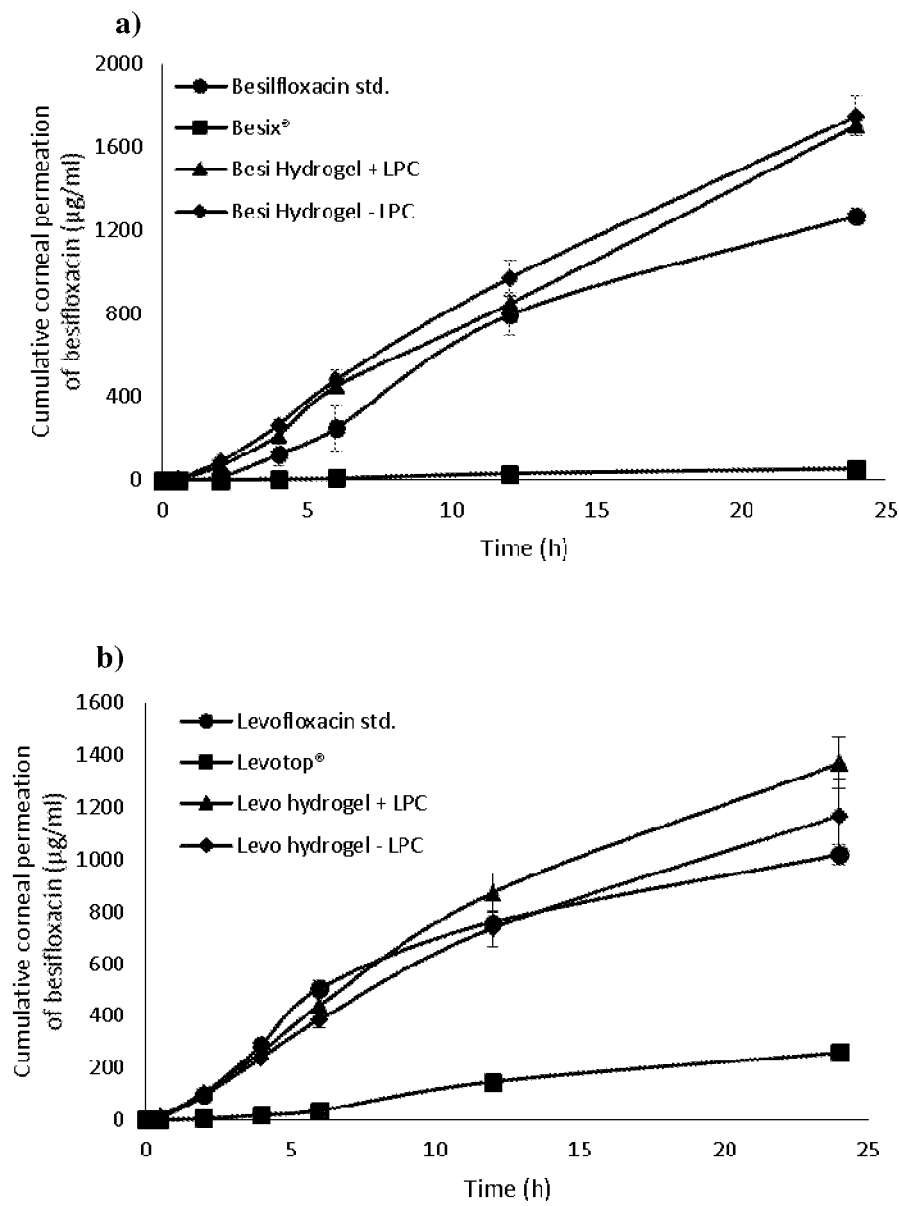
FIG. 3 illustrates ex vivo corneal penetration profiles of (a) besifloxacin from Besix®, hydrogel formulation and free drug solution and (b) levofloxacin from Levotop®, levofloxacin hydrogel and free drug solution after 24 h across excised human cornea.
Figure 4:
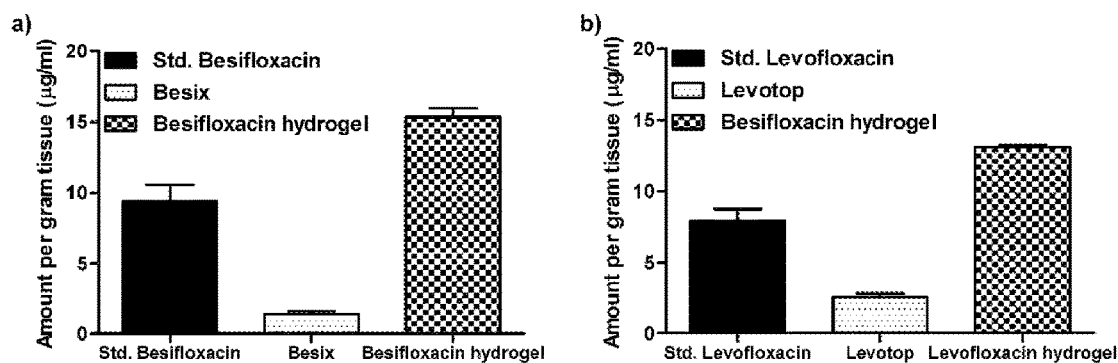
FIG. 4 illustrates ex vivo corneal tissue concentrations of (a) besifloxacin and (b) levofloxacin formulations after 0.5 h incubation.

The average thickness of human cornea used for in-vitro studies was found to be 597.3±40.8 µm. The average transepithelial electrical resistance (TEER) of intact cornea was 2.6±0.4 kΩ. Table 2 shows the corneal TEER values after application of different formulations. Table 3 shows permeation parameters of different formulations of besifloxacin and levofloxacin. In general, lag time was significantly reduced upon application of hydrogel compared with marketed products. The lag time for Besix® and Levotop® was 1.25±0.09 and 1.42±0.04 h, respectively. Hydrogel formulations of besifloxacin and levofloxacin reduced the lag time to 0.92±0.16 and 0.56±0.01 h, respectively. The besifloxacin and levofloxacin hydrogel formulations showed significantly (p<0.05) greater flux of 84.08±13.50 and 77.02±3.71 µg/cm²/h, respectively compared with Besix® (1.86±0.74 µg/cm²/h) and Levotop® (7.85±1.14 µg/cm²/h). It was found that addition of lysophosphotidyl choline improved the flux up to 10% for besifloxacin and 20% for levofloxacin hydrogels. FIG. 3 shows the cumulative corneal permeation of besifloxacin and levofloxacin from hydrogel formulations. Cumulative amount of besifloxacin permeation across cornea after application using hydrogel formulation, Besix® and free drug solutions was found to be 1747±95, 55±12 and 1267±38 µg, respectively after 24 h. Similarly, the corneal tissue concentration was found to be 258±37, 16±1, and 398±50 µg/gram of tissue for hydrogel formulation, Besix® and free drug solution.

In the case of levofloxacin, the cumulative corneal penetration from hydrogel formulation, Levotop® and free drug solution was found to be 1369±98, 259±13 and 1019±144 µg, respectively. The corneal tissue concentration was found to be 305±38, 130±17 and 251±13 µg/gram of tissue for hydrogel formulation, Levotop® and free drug solution, respectively. In addition, it was found that the hydrogel formulations had significantly (p<0.05) higher diffusion and permeability coefficients compared to the marketed products.

TABLE 2

Transepithelial electrical resistance (TEER) before and after application of besifloxacin and levofloxacin formulations

| | Intact cornea | Standard drug solution | Besix ®/ Levotop ® | Hydrogel + LPC | Hydrogel − LPC |
|---|---|---|---|---|---|
| Besifloxacin Formulation | 2.60 ± 0.42 | 2.17 ± 0.09 | 2.37 ± 0.11 | 1.91 ± 0.10* | 1.72 ± 0.15* |
| Levofloxacin Formulation | | 2.22 ± 0.16 | 2.27 ± 0.13 | 2.12 ± 0.07 | 2.20 ± 0.16 |

*Significance between marketed preparation and hydrogel formulation (p < 0.01); Values are expressed in kΩ.

TABLE 3

Corneal permeation parameters for besifloxacin and levofloxacin preparations

| Formulation | Description | Lag time (h) | Flux (µg/cm²/h) | Cumulative amount permeated (µg/cm²) | Diffusion coefficient (×10⁻³) | Permeability coefficient (×10⁻³, cm²/h) |
|---|---|---|---|---|---|---|
| Besifloxacin Std. | Besifloxacin solution | 1.22 ± 0.39 | 36.80 ± 13.99 | 1267.42 ± 37.56 | 21.34 | 15.57 |
| Levofloxacin Std. | Levofloxacin solution | 1.23 ± 0.22 | 101.52 ± 4.16 | 1019.18 ± 144.14 | 44.57 | 36.66 |
| Besix ® | Marketed preparation | 1.25 ± 0.09 | 1.86 ± 0.74 | 55.13 ± 12.04 | 21.04 | 0.62 |
| Levotop ® | Marketed preparation | 1.421 ± 0.04 | 7.85 ± 1.14 | 258.73 ± 12.99 | 34.75 | 3.47 |
| Besifloxacin hydrogel + LPC | Besifloxacin in hydrogel containing 3% PVA + 1.0% PVP + 1% Chi + 0.05% LPC | 0.921 ± 0.16 | 84.08 ± 13.5 | 1747.18 ± 94.62 | 31.59 | 20.91 |

TABLE 3-continued

Corneal permeation parameters for besifloxacin and levofloxacin preparations

| Formulation | Description | Lag time (h) | Flux (μg/cm²/h) | Cumulative amount permeated (μg/cm²) | Diffusion coefficient (×10⁻³) | Permeability coefficient (×10⁻³, cm²/h) |
|---|---|---|---|---|---|---|
| Besifloxacin hydrogel – LPC | Besifloxacin in hydrogel containing 3% PVA + 1.0% PVP + 1% Chi | 0.764 ± 0.19 | 77.34 ± 2.20 | 1920.36 ± 49.01 | 31.56 | 29.93 |
| Levofloxacin hydrogel + LPC | Levofloxacin in hydrogel containing 1% PVA + 0.5% PVP + 0.5% Chi + 0.05% LPC | 0.562 ± 0.01 | 77.02 ± 3.71 | 1368.77 ± 98.48 | 27.31 | 32.38 |
| Levofloxacin hydrogel – LPC | Levofloxacin in hydrogel containing 1% PVA + 0.5% PVP + 0.5% Chi | 0.636 ± 0.011 | 62.33 ± 13.29 | 1168.56 ± 139.33 | 30.13 | 29 |

Evaluation of Antibacterial Activity in Ex Vivo Corneal Infection Model

Human corneas were incubated in antibiotic free DMEM media overnight at 37° C. Next day, cornea was washed thrice with sterile PBS and $10^8$ cells of *Staphylococcus aureus* were injected (using a 26-gauge needle) intra-stromally. After 24 h incubation at 37° C., the infected corneas were washed again with PBS and used for further studies. The infection-free corneas were used as controls (Pinnock, et. al, 2017).

Infected cornea was washed, and a metal ring was placed on the corneoscleral button, creating a watertight seal. Drug formulations (0.4%) were added to the center of the ring and incubated for 0.5 and 1.5 h at 37° C. Later, the corneas were washed thoroughly with PBS to remove the excess formulation and incubated for 24 h at 37° C. The cornea was then homogenized, and the resulting suspension was serially diluted. A 10 μl sample was spotted on agar plates at $10^{-5}$, $10^{-6}$, $10^{-7}$, $10^{-8}$ dilutions for colony enumeration. The colonies were counted visually and expressed in colony forming units (CFU) using Equation 2.

$$CFU \text{ per } ml = \frac{\text{number of colonies} \times \text{dilution factor}}{\text{volume of culture plated}} \quad (2)$$

All the results are presented as mean±standard deviation. Statistical analysis was performed using analysis of variance (ANOVA) (Graphpad Prism, V5) and p<0.05 was considered to be minimum level of significance.

Antibacterial Activity of Besifloxacin and Levofloxacin Hydrogel Formulations

Figure 5:
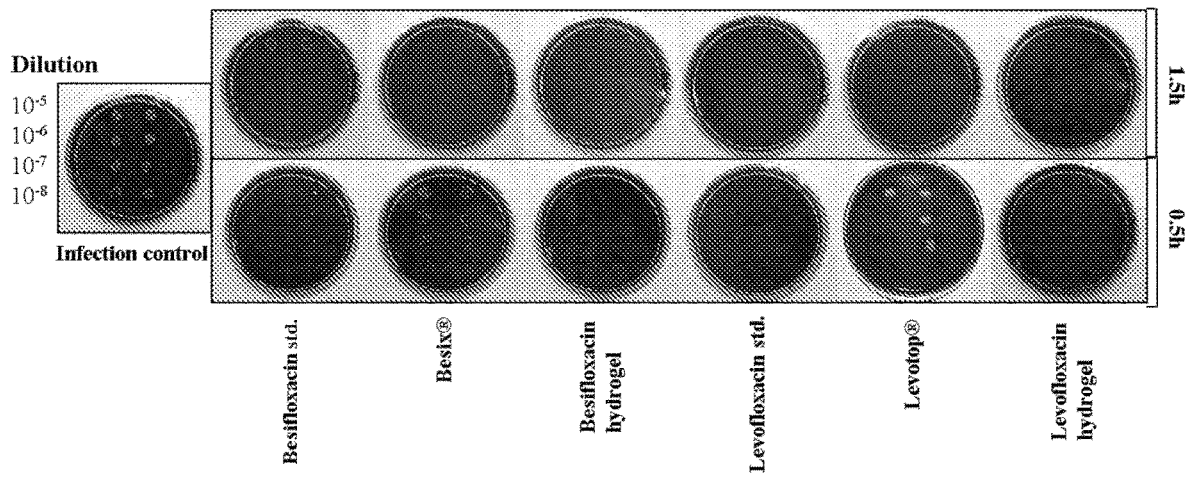
FIG. 5 illustrates antimicrobial activity of besifloxacin and levofloxacin formulations against *S. aureus*, ATCC 25923 infected cornea after incubation for 1.5 and 0.5 h.

The antibacterial activity of drugs loaded in hydrogel formulations was evaluated against *Staphylococcus aureus* (ATCC 25923) infected human cornea (n=3). FIG. 5 and Table 4 show concentration dependent inhibition of bacterial growth after incubation of infected cornea for 30 min with drug formulations. Hydrogel formulations of both besifloxacin and levofloxacin were effective in antibacterial activity where only $0.1 \times 10^9$ CFU/ml was recorded, when compared with $8.0 \times 10^9$ and $2.8 \times 10^9$ CFU/ml after incubation with Besix® and Levotop®, respectively.

TABLE 4

| Formulation | CFU/ml (×10⁹) |
|---|---|
| Infection control | 28.2 ± 4.29 |
| Besifloxacin Std. | 2.5 ± 0.82 |
| Besix ® | 8.0 ± 3.27 |
| Besifloxacin hydrogel | 0.16 ± 0.24** |
| Levofloxacin Std. | 8.3 ± 5.10 |
| Levotop ® | 2.8 ± 1.43 |
| Levofloxacin hydrogel | 0.16 ± 0.24 |

**Significance between marketed and hydrogel formulation (p < 0.05)
CFU/ml = (no. of colonies × dilution factor)/volume of culture plated.
The values in table are from $10^{-7}$ dilution Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus, it is intended that the present disclosure include such modifications and variations and their equivalents. Other objects, features and aspects of the present invention are disclosed in or are obvious from, the following detailed description. It is to be understood by one of ordinary skill in the art that the present discussion is a description of exemplary embodiments only and is not to be construed as limiting the broader aspects of the present disclosure.

The invention claimed is:

1. A pharmaceutical composition comprising a therapeutically effective amount of a fluoroquinolone antibiotic, chitosan, polyvinyl alcohol and polyvinylpyrrolidone; wherein the composition comprises fluoroquinolone antibiotic in an amount from about 0.01 to about 1% w/v; chitosan in an amount from about 0.2 to about 3% w/v; polyvinyl-alcohol in an amount from about 0.2 to about 8% w/v; and polyvinylpyrrolidone in an amount from about 0.5 to about 8% w/v; wherein the composition is a hydrogel.

2. The pharmaceutical composition as claimed in claim 1, wherein the composition further comprises one or more permeation enhancers.

3. The pharmaceutical composition as claimed in claim 2, wherein the permeation enhancer is lysophosphatidilo lipid.

4. The pharmaceutical composition as claimed in claim 2, wherein the permeation enhancer is lysophosphatidylcholine.

5. The pharmaceutical composition as claimed in claim 4, wherein lysophosphatidylcholine is present in an amount from about 0.01 to about 2% w/v.

6. The pharmaceutical composition as claimed in claim 5, wherein the composition comprises:
fluoroquinolone antibiotic in an amount from about 0.3 to about 0.6% w/v;
chitosan in an amount from about 0.5 to about 2% w/v;
polyvinylalcohol in an amount from about 0.5 to about 5% w/v;
polyvinylpyrrolidone in an amount from about 0.5 to about 5% w/v; and
lysophosphatidylcholine in an amount from about 0.05 to about 0.5% w/v.

7. The pharmaceutical composition as claimed in claim 1, wherein the fluoroquinolone antibiotic is selected from balofloxacin, besifloxacin, cinoxacin, ciprofloxacin, clinafloxacin, danofloxacin, delafloxacin, difloxacin, enoxacin, enrofloxacin, fleroxacin, flumequine, gatifloxacin, gemifloxacin, grepafloxacin, ibafloxacin, JNJ-Q2, levofloxacin, lomefloxacin, marbofloxacin, moxifloxacin, nadifloxacin, nalidixic acid, nemonoxacin, norfloxacin, ofloxacin, orbifloxacin, oxilinic acid, pazufloxacin, pefloxacin, piromidic acid, pipemidic acid, prulifloxacin, rosoxacin, rufloxacin, sarafloxacin, sparfloxacin, sitafloxacin, temafloxacin, tosufloxacin, trovafloxacin, or a pharmaceutically acceptable salt or a stereoisomer thereof.

8. The pharmaceutical composition as claimed in claim 1, wherein the fluoroquinolone antibiotic is besifloxacin or levofloxacin.

9. The pharmaceutical composition as claimed in claim 1, wherein the composition further comprises a pharmaceutically acceptable carrier or excipient.

10. A method for treating an ocular condition caused by Gram-positive or Gram-negative bacteria in a subject comprising administering to target site of an eye of the subject a pharmaceutical composition as claimed in claim 1.

11. The method as claimed in claim 10, wherein the ocular condition caused by Gram-positive or Gram-negative bacteria is selected from a group comprising blepharitis, conjunctivitis, keratitis, and endophthalmitis.

12. A mucoadhesive ophthalmic drug delivery system comprising the pharmaceutical composition as claimed in claim 1.

13. The method of claim 10, comprising delivering the fluoroquinolone antibiotic through ocular tissue of the eye of the subject.

14. The method as claimed in claim 13, wherein the ocular tissue is corneal tissue.

15. A kit comprising the pharmaceutical composition as claimed in claim 1.

16. The method of claim 10, wherein the pharmaceutical composition comprises:
the fluoroquinolone antibiotic in an amount from about 0.3 to about 0.6% w/v;
the chitosan in an amount from about 0.5 to about 2% w/v;
the polyvinylalcohol in an amount from about 0.5 to about 5% w/v; and
the polyvinylpyrrolidone in an amount from about 0.5 to about 5% w/v.

17. The method of claim 16, wherein the pharmaceutical composition further comprises lysophosphatidylcholine in an amount from about 0.05 to about 0.5% w/v.

18. The method of claim 10, wherein the fluoroquinolone antibiotic is besifloxacin or levofloxacin.

* * * * *

UNITED STATES PATENT AND TRADEMARK OFFICE
CERTIFICATE OF CORRECTION

PATENT NO. : 12,042,500 B2
APPLICATION NO. : 17/044922
DATED : July 23, 2024
INVENTOR(S) : S. Gade et al.

Page 1 of 1

It is certified that error appears in the above-identified patent and that said Letters Patent is hereby corrected as shown below:

In the Claims

Column 16, Lines 59-60 (Claim 1) please change "polyvinylalcohol" to -- polyvinyl-alcohol --
Column 17, Line 12 (Claim 6) please change "polyvinylalcohol" to -- polyvinyl-alcohol --
Column 18, Line 25 (Claim 16) please change "polyvinylalcohol" to -- polyvinyl-alcohol --

Signed and Sealed this
Twenty-first Day of January, 2025

Coke Morgan Stewart
*Acting Director of the United States Patent and Trademark Office*